United States Patent [19]
Au-Young

[11] Patent Number: 5,856,136
[45] Date of Patent: Jan. 5, 1999

[54] HUMAN STEM CELL ANTIGENS

[75] Inventor: Janice Au-Young, Berkeley, Calif.

[73] Assignee: Incyte Pharmaceuticals, Inc., Palo Alto, Calif.

[21] Appl. No.: 675,508

[22] Filed: Jul. 3, 1996

[51] Int. Cl.$^6$ .......................... C12N 15/12; C12N 15/70; C12N 15/74; C12N 15/85
[52] U.S. Cl. .................. 435/69.3; 435/252.3; 435/320.1; 435/325; 536/23.5
[58] Field of Search ........................ 536/23.5; 435/320.1, 435/240.2, 69.3, 243, 252.3, 325

[56] References Cited

U.S. PATENT DOCUMENTS 5,468,612  11/1995  Cohen et al. ................................ 435/6

FOREIGN PATENT DOCUMENTS

WO 97/18224  5/1997  WIPO .

OTHER PUBLICATIONS

Mao, M. et al., "RIG–E, a human homolog of the murine Ly–6 family, is induced by retinoic acid during the differentiation of acute promyelocytic leukemia cell", *Proc. Natl. Acad. Sci. USA*, 93: 5910–5914 (1996).

Triglia T, et al. "A procedure for in vitro amplification of DNA segments that lie outside the boundaries of known sequences." Nucl. Acids Res. 16: 8186–8187, 1988.

Fleming et al., "Characterization of Two Novel Ly–6 Genes", (1993), *J Immunol*, vol. 150(12), pp. 5379–5390.

Blake et al., "Ly–6 Is Kidney s Widely Expressed on Tubular Epithelium and Vascular Endothelium and is Upregulated by Interferon Gamma", (1993), J Am *Soc Nephrol*, vol. 4(5), pp. 1140–1150.

Godfrey et al., "Thymic shared antigen–1. A Novel Thymocyte Marker Discriminating Immature from Mature Thymocyte Subsets", (1992), *J Immunol*, vol. 148, pp. 2006–2011.

MacNeil et at., "Isolation of a cDNA Encloding Thymic Shared Antigen–1", *J Immunol*, vol. 151, pp. 6913–6923.

Fleming et al., "Multiple Glycosylphosphatidylinositol–Anchored Ly–6 Molecules and Transmembrane Ly–6E Mediate Inhibition of IL–2 Production", (1994), *The Journal of Immunology*, vol. 153, pp. 1955–1962.

Classon et al., "Mouse stem cell antigen Sca–2 is a member of the Ly–6 of cell surface proteins", (1994), *Proc. Natl. Acad. Sci.*, vol. 91, pp. 5296–5300.

Lin et al., "Characterization of A1, a Novel Hemopietic–Specific Early–Response Gene with Sequence Similarity to bcl–2", (1993), *The Journal of Immunology*, vol. 151, pp. 1979–1988.

Katz et al., "An Association Between High Ly–6A/E Expression on Tumor Cells and a Highly Malignant Phenotype", (1994), *Int. J. Cancer*, vol. 59, pp. 684–691.

Terstappen et al., "Assessment of Hematopoietic Cell Differentiation by Multidimensional Flow Cytometry", (1993), Journal of Hematotherapy, vol. 2, pp. 431–447.

Classon, B.J. and Coverdale, L., (Direct Submission) (1996)), GenBank Sequence Database, National Center for Biotechnology Information, National Library of Medicine, Building 38A, Room 8N805, Bethesda, MD 20894.

Constanzi, C. And Pehrson, J.R. (GI 1711126), GenBank Sequence Database (Accession U79139), National Center for Biotechnology Information, National Library of Medicine, Methesda, Maryland 20894.

*Primary Examiner*—David T. Fox
*Assistant Examiner*—Amy J. Nelson
*Attorney, Agent, or Firm*—Lucy J. Billings

[57] ABSTRACT

The present invention provides polynucleotides encoding stem cell antigens, the partial sequences for which were initially isolated from THP-1 and bladder tumor cDNA libraries and which identify and encode novel human stem cell antigens. The invention provides for genetically engineered expression vectors and host cells comprising the nucleic acid sequences encoding the stem cell antigens.

5 Claims, 7 Drawing Sheets

```
                   9              18              27              36              45              54
5' NAG GAN GGT GGG GGA CCC ANG GGT CCA GAG CGC AGT TCG GGT CGG AGC TYC GWC 63              72              81              90              99             108
   CAG GCT GCT GGT ACC TGC GTC CGC CCG GCG AGC AGG ACA GGC TGC TTT GGT TTG 117             126             135             144             153             162
   TGA CCT CCA GGC AGG ACG GCC ATC CTC TCC AGA ATG AAG ATC TTC TTG CCA GTG
                                                      M   K   I   F   L   P   V 171             180             189             198             207             216
   CTG CTG GCT GCC CTT CTG GGT GTG GAG CGA GCC AGC TCG CTG ATG TGC TTC TCC
    L   L   A   A   L   L   G   V   E   R   A   S   S   L   M   C   F   S 225             234             243             252             261             270
   TGC TTG AAC CAG AAG AGC AAT CTG TAC TGC CTG AAG CCG ACC ATC TGC TCC GAC
    C   L   N   Q   K   S   N   L   Y   C   L   K   P   T   I   C   S   D 279             288             297             306             315             324
   CAG GAC AAC TAC TGC GTG ACT GTG TCT GCT AGT GCC GGC ATT GGG AAT CTC GTG
    Q   D   N   Y   C   V   T   V   S   A   S   A   G   I   G   N   L   V 333             342             351             360             369             378
   ACA TTT GGC CAC AGC CTG AGC AAG ACC TGT TCC CCG GCC TGC CCC ATC CCA GAA
    T   F   G   H   S   L   S   K   T   C   S   P   A   C   P   I   P   E 387             396             405           · 414             423             432
   GGC GTC AAT GTT GGT GTG GCT TCC ATG GGC ATC AGC TGC TGC CAG AGC TTT CTG
    G   V   N   V   G   V   A   S   M   G   I   S   C   C   Q   S   F   L 441             450             459             468             477             486
   TGC AAT TTC AGT GCG GCC GAT GGC GGG CTG CGG GCA AGC GTC ACC CTG CTG GGT
    C   N   F   S   A   A   D   G   G   L   R   A   S   V   T   L   L   G 495             504             513             522             531
   GCC GGG CTG CTG CTG AGC CTG WTG CCG GCC CTG CTG CGG TTT GGC CCC TGA  3'
    A   G   L   L   L   S   L   X   P   A   L   L   R   F   G   P   *
```

FIGURE 1

```
                9               18              27              36              45              54
5' GTG ACC ATG AAG GCT GTG CTG CTT GCC CTG TTG ATG GCA GGC TTG GCC CTG CAG
   V   T   M   K   A   V   L   L   A   L   L   M   A   G   L   A   L   Q 63              72              81              90              99              108
   CCA GGC ACT GCC CTG CTG TGC TAC TCC TGC AAA GCC CAG GTG AGC AAC GAG GAC
   P   G   T   A   L   L   C   Y   S   C   K   A   Q   V   S   N   E   D 117             126             135             144             153             162
   TGC CTG CAG GTG GAG AAC TGC ACC CAG CTG GGG GAG CAG TGC TGG ACC GCG CGC
   C   L   Q   V   E   N   C   T   Q   L   G   E   Q   C   W   T   A   R 171             180             189             198             207             216
   ATC CGC GCA GTT GGC CTC CTG ACC GTC ATC AGC AAA GGC TGC AGC TTG AAC TGC
   I   R   A   V   G   L   L   T   V   I   S   K   G   C   S   L   N   C 225             234             243             252             261             270
   GTG GAT GAC TCA CAG GAC TAC TAC GTG GGC AAG AAG AAC ATC ACG TGC TGT GAC
   V   D   D   S   Q   D   Y   Y   V   G   K   K   N   I   T   C   C   D 279             288             297             306             315             324
   ACC GAC TTG TGC AAC GSC AGC GGG GCC CAT GCC CTG CAG CCG GCT GCC GCC ATC
   T   D   L   C   N   X   S   G   A   H   A   L   Q   P   A   A   A   I 333             342             351             360             369             378
   CTT GCG CTG CTC CCT GCA CTC GGC CTG CTG CTC TGG GGA CCC GGC CAG CTA TAG
   L   A   L   L   P   A   L   G   L   L   L   W   G   P   G   Q   L   *

387             396             405             414             423             432
   GCT CTG GGG GGC CCC GMT GCA GCC CAC ACT GGG TGT GGT GCC CCA AGG CCT CTG
   A   L   G   G   P   X   A   A   H   T   G   C   G   A   P   R   P   L 441             450             459             468             477             486
   TGS CAC TCC TMA CAG ACC TGG GCC CAG TGG GAG SCT GTC TCT NGG TTC CTG AGG
   X   H   S   X   Q   T   W   A   Q   W   E   X   V   S   X   F   L   R

CAC ATC CT 3'
   H   I
```

FIGURE 2

```
  1  M - - - - - - K I F L P V L L A A L L G V E R A S S L M C F   scah-1
  1  M S A T S N M R V F L P V L L A A L L G M E Q V H S L M C F   GI 434660
  1  M S T T S S M R V F S I V L Q A H L L G V E L V P S L I C S   GI 1199651
  1  M - - - - - - K A V L L A L L M A G L A L Q P G T A L L C Y   scah-2
  1  M - - - - - - K A F L F A V L A A V L C V E R A H T L I C F   GI 509840

25  S C L N Q K S N L Y C L K P T I C S D Q D N Y C V T V S A S   scah-1
 31  S C T D Q K N N I N C L W P V S C Q E K D H Y C I T L S A A   GI 434660
 31  S C T H Q K S N I N P P W P V A C K D T G N Y C I M L F S A   GI 1199651
 25  S C K A Q V S N E D C L Q V E N C T Q L G E Q C W T A R I R   scah-2
 25  S C S D A S S N W A C L T P V K C A E N E E H C V T T Y V G   GI 509840

55  A G I G N L V T F G H S L S K T C S P A C P I P E - G V N V   scah-1
 61  A G F G N - V N L G Y T L N K G C S P I C P S E N V N L N L   GI 434660
 61  V G F G N - V N L G Y T L N T G C S Q S C P H E N I N I N P   GI 1199651
 55  A V - - G L L T V - - - I S K G C S L N C V D D S Q D Y Y V   scah-2
 55  V G I G G - - K S G Q S I S K G C S P V C P S A G I N L - -   GI 509840

84  G V A S M G I S C C Q S F L C N F S A D G L R A S V T L       scah-1
 90  G V A S V N S Y C C Q S S F C N F S A A G L G L R A S I P L   GI 434660
 90  G V A S V N S Y - - Q S S F C N F S N A C L                   GI 1199651
 80  G K K N I T - - C C D T D L C N X S G A H - A L Q P A A A I   scah-2
 81  G I A A S V Y C C D S F L C N I S G S S - S V K A S Y A V     GI 509840

114  L G A G L L L S L X P A L L R F G P                           scah-1
120  L G L G L L L S L L - A L L Q L S P                           GI 434660
109                                                               GI 1199651
107  L A - - - L L P A L G L L L W G P G Q L                      scah-2
110  L A L G I L V S F V - Y V L R A R E                           GI 509840
```

Decoration 'Decoration #1': Box residues that match the Consensus exactly.

FIGURE 3

000# HUMAN STEM CELL ANTIGENS

FIELD OF THE INVENTION

The present invention relates to nucleic acid and amino acid sequences of novel human stem cell antigen and to the use of these sequences in the diagnosis, study, prevention and treatment of disease.

BACKGROUND OF THE INVENTION

Sca-2 is a member of the LY-6 family, a group of small cysteine rich proteins which are widely expressed on the surface of lymphoid cells. These proteins are anchored to the cell membrane by a glycosylphosphotidyl-inositol (GPI) moiety and show conserved protein sequence important for tertiary structure. The general structure seen within the LY-6 family resembles that of the receptor for a urokinase-type plasminogen activator and the alpha-neurotoxins isolated from snake venoms (Fleming T J et al (1993) J Immunol 150:5379–90; Ploug M and V Ellis (1994) FEBS Lett 349:163–8).

Intrathymic T cell precursors express Sca-2. In fact, the progeny of the intrathymic precursor cells continue to express Sca-2 until they transition from blast cells to small cells. During this transition, expression of Sca-2 is down-regulated. In contrast, Sca-2 is not expressed on the hematopoietic stem cells of the bone marrow which give rise to T cell precursors or on mature thymocytes and peripheral T cells; however, peripheral B cells are Sca-2 positive.

In studies involving interferon gamma induced murine kidney, Blake P G et al. (1993; J Am Soc Nephrol 4:1140–50) showed a high level of expression of LY-6s associated with lupus nephritis. Such expression makes these molecules either candidates or targets for alloresponses and autoimmune disease. Upregulation of LY-6 was also associated with mercuric chloride nephropathy.

Sca-2 is also related to the mouse thymocyte marker, TSA-1 (Godfrey D I et al. (1992) J Immunol 148:2006–11). TSA-1 is expressed on immature thymocytes and a subset of thymic medullary epithelial cells and appears to be a unique molecule for discriminating between mature and immature thymocytes. TSA-1 is distinct from CD5, CD11a/18, Thy-1, LY6A/E, LY6C, ThB, CD25, and CD44. TSA-1 appears to play a role during positive selection in the transition from CD4+CD8+ thymocytes to the mature CD4+CD8– and CD4–CD8+ subsets (MacNeil I et al. (1993) J Immunol 151:6913–23).

Katz et al(1994; Int J Cancer 59:684–91) showed that LY-6 is highly expressed on non-lymphoid tumor cells originating from a variety of tissues in mice. Upregulation or high expression is correlated with a more malignant phenotype which results in higher efficiency of local tumor production. Since cells with high or low expression show no differences in vitro, it is suggested that micro-environmental factors operating in vivo contribute to malignant phenotype. Katz also noted that antibodies to LY-6 transduce proliferation.

LY-6 proteins also block interleukin 2 (IL-2) secretion (Fleming T J and T R Malek (1994) J Immunol 153:1955–62). IL-2 is an approved anticancer agent and key regulatory hormone in cell-mediated immunity. It stimulates the proliferation of both T and natural killer cells and activates NK cells. In vitro, activated NK cells can directly lyse freshly isolated, solid tumor cells. Fleming also reported that controlled administration of high doses of IL-2 and autologous NK cells (expanded ex vivo) produced favorable responses in patients with metastatic melanoma and renal cell carcinoma.

Understanding the correlations among high expression of Ly-6 family proteins, blocking of IL-2 secretion, and alloresponses or malignancy may allow new approaches to transplantation and treating carcinomas. Identification of novel stem cell antigens provides increased opportunities to develop the diagnostic and pharmacological tools and drugs to intervene in autoimmune diseases, problems arising with allografts and tumor development.

SUMMARY OF THE INVENTION

The present invention discloses novel human stem cell antigens (SCAH), characterized as having homology to Sca-2. Accordingly, the invention features substantially purified SCAH-1 and SCAH-2, encoded by the amino acid sequences of SEQ ID NO:1 and 2, respectively, and having characteristics of the LY-6 family of cysteine rich proteins which are expressed on the surface of lymphoid cells.

One aspect of the invention features isolated and substantially purified polynucleotides which encode SCAH-1 and SCAH-2. In a particular aspect, the polynucleotide sequence encoding SCAH-1 is the nucleic acid sequence of SEQ ID NO:3 and the polynucleotide sequence encoding SCAH-2 is the nucleic acid sequence of SEQ ID NO:4. In addition, the invention features a polynucleotide sequence that hybridizes under stringent conditions to SEQ ID NO:3, and a polynucleotide sequence that hybridizes under stringent conditions to SEQ ID NO:4.

The nucleic acid sequences, oligonucleotides, peptide nucleic acids (PNA), fragments, portions or antisense molecules thereof, may be used in diagnostic assays of body fluids or biopsied tissues to detect expression levels of polynucleotides encoding SCAH-1 or SCAH-2. For example, nucleic acid sequences designed from SEQ ID NO:3 can be used to detect the presence of mRNA transcripts in a patient or to monitor modulation of the transcripts during treatment.

The present invention relates, in part, to the inclusion of the polynucleotides encoding SCAH-1 or SCAH-2 in an expression vector which can be used to transform host cells or organisms. Such transgenic hosts are useful for the production of SCAH proteins.

The invention further provides diagnostic assays and kits for the detection of naturally occurring SCAH-1 or SCAH-2. It provides for the use of substantially purified SCAH-1 or SCAH-2 as a positive control and to produce anti-SCAH-1 or SCAH-2 antibodies which can be used to quantitate the amount of SCAH proteins in human body fluids or biopsied tissues. These SCAH proteins can also be used to produce antagonists which will bind to SCAH molecules on the surface of tumor cells in vivo or in vitro.

Substantially purified SCAH-1 or SCAH-2 or their fragments may be useful as pharmaceutical compositions. For example, they may be used to inhibit or reverse the development of tumors.

The invention also relates to pharmaceutical compositions comprising antisense molecules capable of disrupting expression of genomic sequences, and agonists, antibodies, antagonists or inhibitors of the SCAH-1 or SCAH-2. These compositions are useful for the prevention or treatment of conditions associated with the presence or the expression of SCAH-1 or SCAH-2.

BRIEF DESCRIPTION OF THE FIGURES

FIG. 1 shows the assembled nucleic acid sequence (SEQ ID NO:3) and deduced amino acid sequence (SEQ ID NO:1)

of the human stem cell antigen homolog, SCAH-1 produced using MACDNASIS software (Hitachi Software Engineering Co Ltd).

FIG. 2 shows the assembled nucleic acid sequence (SEQ ID NO:4) and deduced amino acid sequence (SEQ ID NO:2) of the human stem cell antigen homolog, SCAH-2 produced using MACDNASIS software (Hitachi Software Engineering Co Ltd).

FIG. 3 shows the amino acid sequence alignments among SCAH-1 (SEQ ID NO:1), GI 434660 (SEQ ID NO:5), GI 1199651 (SEQ ID NO:6), SCAH-2 (SEQ ID NO:2), and GI 509840 (SEQ ID NO:20) produced using the multisequence alignment program of DNASTAR software (DNASTAR Inc, Madison Wis.).

Figure 4:
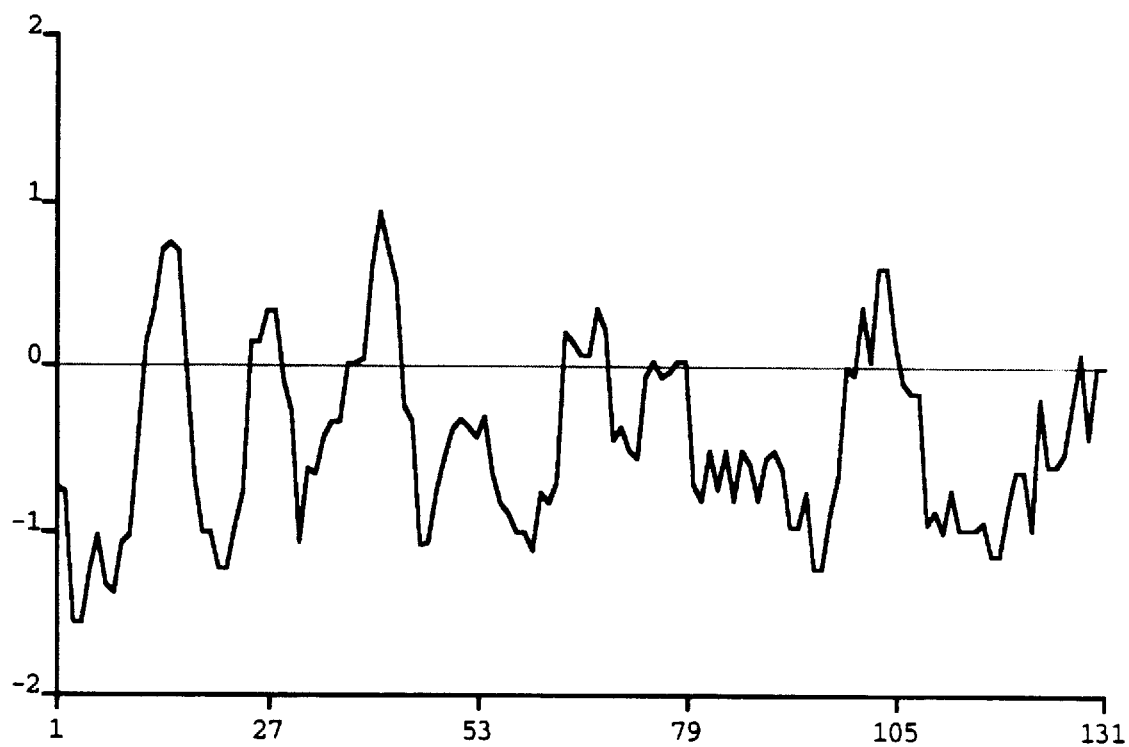
Figure 5:
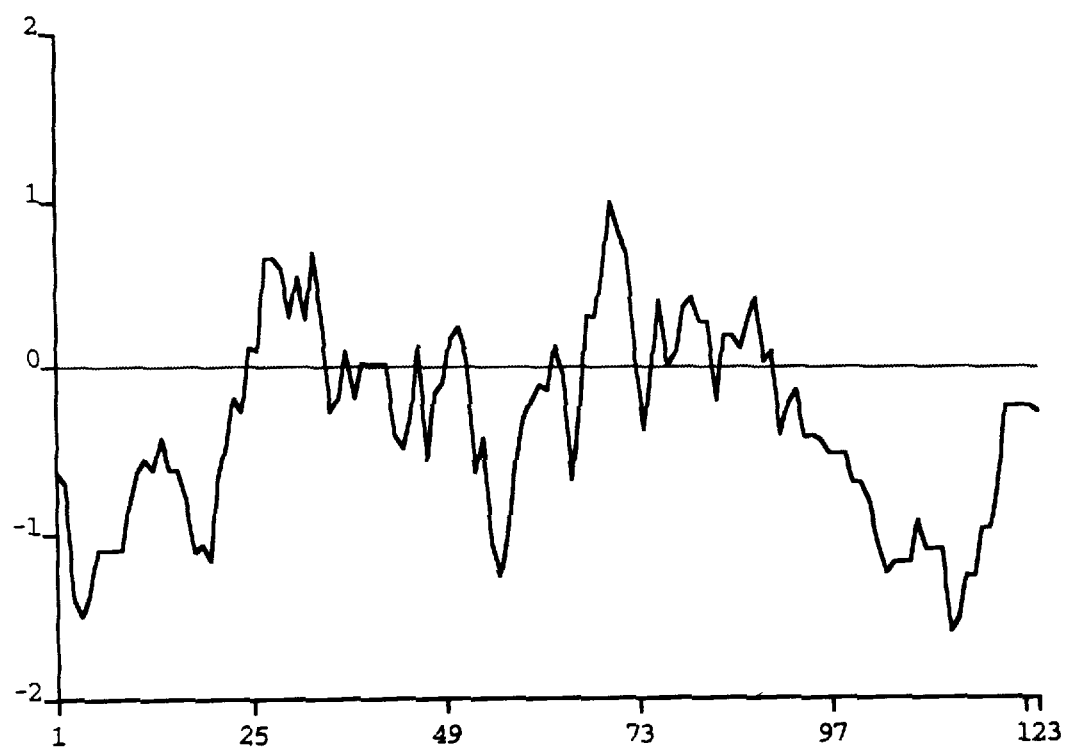

FIG. 4 shows the hydrophobicity plot for SCAH-1 (SEQ ID NO:1) generated using MACDNASIS software. In FIGS. 4 and 5, the X axis reflects amino acid position, and the negative Y axis, hydrophobicity.

FIG. 5 shows the hydrophobicity plot for SCAH-2 (SEQ ID NO:2) generated using MACDNASIS software.

Figure 6:
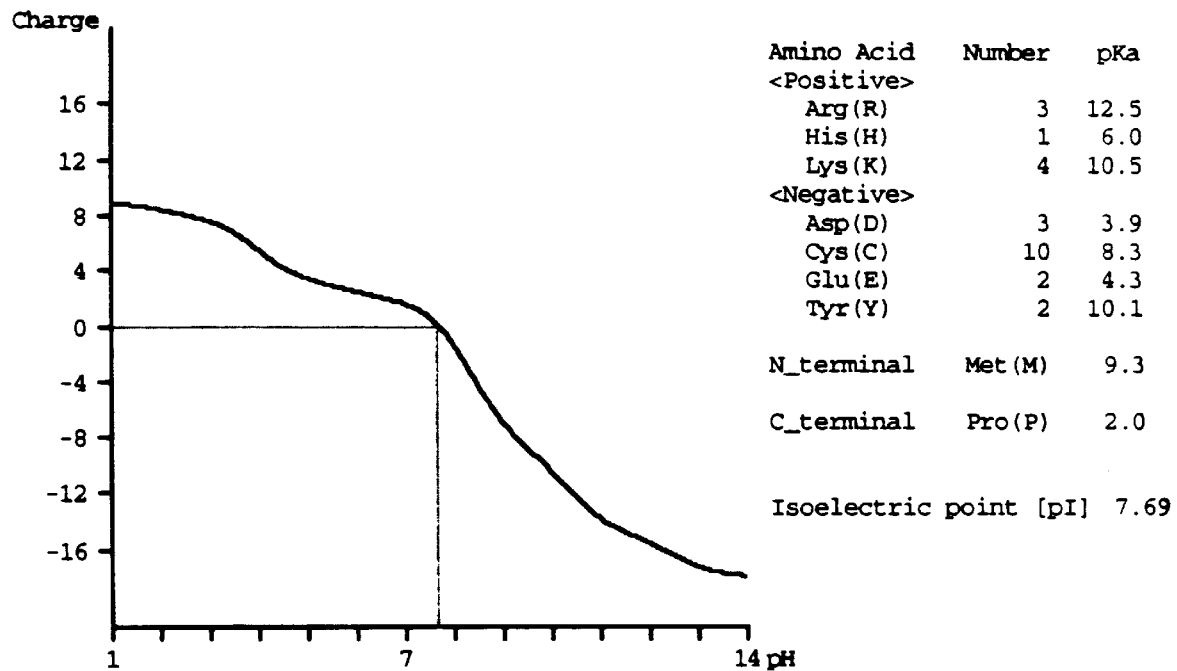

FIG. 6 shows an isoelectric plot for SCAH-1 (SEQ ID NO:1) generated using MACDNASIS software.

Figure 7:
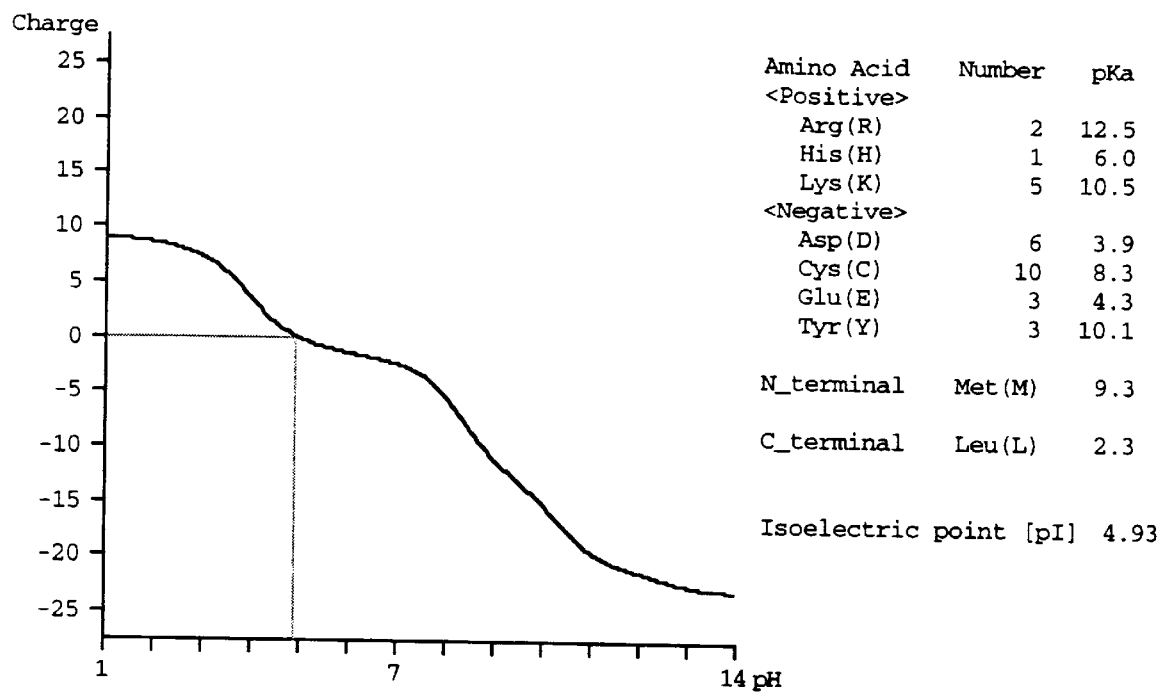

FIG. 7 shows an isoelectric plot for SCAH-2 (SEQ ID NO:2) generated using MACDNASIS software.

DETAILED DESCRIPTION OF THE INVENTION

Definitions

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, "amino acid sequence" as used herein refers to a peptide or protein sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen P E et al (1993) Anticancer Drug Des 8:53–63).

As used herein, SCAH refers to the amino acid sequence of SCAH from any species, particularly mammalian, including bovine, ovine, porcine, murine, equine, and preferably human, in a naturally occurring form or from any source whether natural, synthetic, semi-synthetic or recombinant. As used herein, "naturally occurring" refers to an amino acid sequence which is found in nature.

A "variant" of SCAH may have an amino acid sequence that is different by one or more amino acid "substitutions". The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNASTAR software.

The term "biologically active" refers to a SCAH having structural, regulatory or biochemical functions of the naturally occurring SCAH. Likewise, "immunologically active" defines the capability of the natural, recombinant or synthetic SCAH, or any oligopeptide thereof, to induce a specific immune response in appropriate animals or cells and to bind with specific antibodies.

The term "derivative" as used herein refers to the chemical modification of the nucleic acid sequence or the encoded protein. Illustrative of such modifications would be replacement of hydrogen by an alkyl, acyl, or amino group. A SCAH derivative would encode a polypeptide which retains essential biological characteristics of natural SCAH.

As used herein, the term "substantially purified" refers to molecules, either nucleic or amino acid sequences, that are removed, isolated or separated from their natural environment and are at least 60% free, preferably 75% free, and most preferably 90% free from other components with which they are naturally associated.

Description

The present invention relates to novel human stem cell antigen homologs, SCAH-1 and SCAH-2, which were initially identified among the partial cDNAs from a THP-1 library (THP1PLB02) and bladder tumor library (BLADTUT02), respectively, and to the use of the disclosed nucleic acid and amino acid sequences in the study, diagnosis, prevention and treatment of disease. The nucleic acid sequence encoding a portion of the novel stem cell antigen homolog-1 (designated in lower case, scah-1) was present in stimulated THP-1 and HNT2 cells and in tissues removed from breast, lung, ovary and prostate tumor or adjacent non-tumorous tissues. The nucleic acid sequence encoding a portion of the novel stem cell antigen homolog-2 (designated in lower case, scah-2) was present in tissues removed from bladder tumor and uterus.

The nucleic acid sequence for scah-1 of the present invention was first identified in the partial cDNA, Incyte Clone 155838 (SEQ ID NO: 8), through a computer-generated search for amino acid sequence alignments. The nucleic acid sequence, SEQ ID NO: 3, disclosed herein, encodes the amino acid sequence, SEQ ID NO: 1, designated in upper case, SCAH-1. SEQ ID NO:3 was assembled from the overlapping sequences found in Incyte Clones 72518, 155838, 486681, 604702, 606246, 637479, 641178, 642012, 690697, 728784, 797584, 831396, and 897330 (SEQ ID NOs: 7–19). The present invention is based, in part, on the chemical and structural homology between SCAH and the Sca-2 homologs, GI 494660 and GI 1199651 (Classon B J and L Coverdale (1994) Proc Nat Acad Sci 91:5296–300; Classon B J and L Coverdale (1996) J Immunol 151:1979–88, respectively). SCAH-1 has 25% identity to mouse stem cell antigen-2. The novel SCAH-1 is 131 amino acids long and contains a potential glycosylation site at $N_{99}$.

The nucleic acid sequence for scah-2 of the present invention was first identified in the partial cDNA, Incyte Clone 1312529 (SEQ ID NO:23), through a computer-generated search for amino acid sequence alignments. The nucleic acid sequence, SEQ ID NO:4, disclosed herein, encodes the amino acid sequence, SEQ ID NO:2, designated in upper case, SCAH-2. SEQ ID NO:4 was assembled from the overlapping sequences found in Incyte Clones 588615, 590328, 1312529, 1314679, 1315052 and 1317088 (SEQ ID NOs: 21–26). The present invention is based, in part, on the chemical and structural homology between SCAH-2 and chicken stem cell antigen 2, GI 509840 (SEQ ID NO:20; Petrenko 0 and Enrietto P J (1994) Unpublished). SCAH-2 has 27% identity to chicken stem cell antigen 2, is 123 amino acids long and contains three potential glycosylation sites at $N_{40}$, $N_{83}$, and $N_{96}$.

The amino acid alignments among the stem cell antigens are shown in FIG. 3. Using the numbers for SCAH-1 amino acids at the top of the figure as reference, the following cysteine residues, $C_{23}$, $C_{26}$, $C_{41}$, $C_{48}$, $C_{72}$, and $C_{76}$, and the potential $N_{99}$-linked glycosylation sites are conserved among all five molecules. Such conservation suggests common structural and functional homologies among these proteins.

The SCAH Coding Sequences

The nucleic acid and deduced amino acid sequences of SCAH-1 and SCAH-2 are shown in FIGS. 1 and 2, respectively. In accordance with the invention, any nucleic acid sequence which encodes the amino acid sequence of these molecules can be used to generate recombinant molecules which express SCAH-1 or SCAH-2. In a specific embodiment described herein, the sequence for scah-1 was first isolated as Incyte Clone 155838 from a THP-1 cDNA library (THP1PBL02). Similarly, the sequence for scah-2 was first isolated as Incyte Clone 1312529 from a bladder tumor cDNA library (BLADTUT02).

It will be appreciated by those skilled in the art that as a result of the degeneracy of the genetic code, a multitude of SCAH-encoding nucleotide sequences, some bearing minimal homology to the nucleotide sequences of any known and naturally occurring gene may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring SCAH, and all such variations are to be considered as being specifically disclosed.

Although nucleotide sequences which encode SCAH and its variants are preferably capable of hybridizing to the nucleotide sequence of the naturally occurring scah under appropriately selected conditions of stringency, it may be advantageous to produce nucleotide sequences encoding SCAH or its variants possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding SCAH without altering the encoded amino acid sequences include the production of RNA transcripts having more desirable properties, such as a greater half-life, than transcripts produced from the naturally occurring sequence.

Methods for DNA sequencing are well known in the art and employ such enzymes as the Klenow fragment of DNA polymerase I, SEQUENASE (US Biochemical Corp, Cleveland Ohio), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.).

Methods to extend the DNA sequence from an oligonucleotide primer annealed to the DNA template of interest have been developed for both single-stranded and double-stranded templates. Chain termination reaction products were separated using electrophoresis and detected via their incorporated, labeled precursors. Recent improvements in mechanized reaction preparation, sequencing and analysis have permitted expansion in the number of sequences that can be determined per day. Preferably, the process is automated with machines such as the Hamilton Micro Lab 2200 (Hamilton, Reno Nev.), Peltier Thermal Cycler (PTC200; MJ Research, Watertown Mass.) and the ABI 377 DNA sequencers (Perkin Elmer).

The quality of any particular cDNA library may be determined by performing a pilot scale analysis of the cDNAs and checking for percentages of clones containing vector, lambda or E. coli DNA, mitochondrial or repetitive DNA, and clones with exact or homologous matches to sequences in public databases.

Extending the Polynucleotide Sequence

The polynucleotide sequence of scah may be extended utilizing partial nucleotide sequence and various methods known in the art to detect upstream sequences such as promoters and regulatory elements. Useful nucleotide sequences may be joined to scah in an assortment of cloning vectors, eg, plasmids, cosmids, lambda phage derivatives, phagemids, and the like, that are well known in the art. In general, these vector will contain an origin of replication functional in at least one organism, convenient restriction endonuclease sensitive sites, and selectable markers for the host cell.

Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Parker J D et al (1991; Nucleic Acids Res 19:3055–60), teach walking PCR, a method for targeted gene walking which permits retrieval of unknown sequence. PROMOTERFINDER a new kit available from Clontech (Palo Alto Calif.) uses PCR, nested primers and PROMOTERFINDER libraries to walk in genomic DNA. This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

A new method for analyzing either the size or confirming the nucleotide sequence of sequencing or PCR products is capillary electrophoresis. Systems for rapid sequencing are available from Perkin Elmer, Beckman Instruments (Fullerton Calif.), and other companies. Capillary sequencing employs flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg. GENOTYPER and SEQUENCE NAVIGATOR from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) Anal Chem 65:2851–8).

Expression of the Nucleotide Sequence

In accordance with the present invention, polynucleotide sequences which encode SCAH, fragments of the polypeptide, fusion proteins or functional equivalents thereof may be used in recombinant DNA molecules that direct the expression of SCAH in appropriate host cells. Due to the inherent degeneracy of the genetic code, other DNA sequences which encode substantially the same or a functionally equivalent amino acid sequence, may be used to clone and express SCAH. As will be understood by those of skill in the art, it may be advantageous to produce SCAH-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of SCAH expression or to produce recombinant RNA transcripts having desirable properties, such as a longer half-life, than transcripts produced from naturally occurring sequence.

Also included within the scope of the present invention are polynucleotide sequences that are capable of hybridizing to the nucleotide sequence of FIGS. 1 and 2 under various conditions of stringency. Hybridization conditions are based on the melting temperature (Tm) of the nucleic acid binding complex or probe, as taught in Berger and Kimmel (1987, *Guide to Molecular Cloning Techniques*, Methods in Enzymology, Vol 152, Academic Press, San Diego Calif.) incorporated herein by reference, and confer may be used at a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

The term "hybridization" as used herein shall include "any process by which a strand of nucleic acid joins with a complementary strand through base pairing" (Coombs J (1994) *Dictionary of Biotechnology*, Stockton Press, New York N.Y.). Amplification in polymerase chain reaction technologies is described in Dieffenbach C W and G S Dveksler (1995, *PCR Primer, a Laboratory Manual*, Cold Spring Harbor Press, Plainview N.Y.).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring SCAH.

A "substitution" results from the replacement of one or more nucleotides or amino acids by different nucleotides or amino acids, respectively.

Altered scah nucleic acid sequences which may be used in accordance with the invention include deletions, insertions or substitutions of different nucleotides resulting in a polynucleotide that encodes the same or a functionally equivalent SCAH. The protein may also show deletions, insertions or substitutions of amino acid residues which produce a silent change and result in a functionally equivalent SCAH. Deliberate amino acid substitutions may be made on the basis of similarity in polarity, charge, solubility, hydrophobicity, hydrophilicity, and/or the amphipathic nature of the residues as long as the biological activity of SCAH is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of scah. As used herein, an "allele" or "allelic sequence" is an alternative form of scah. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

The nucleotide sequences of the present invention can be engineered in order to alter a scah coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant scah sequence may be ligated to a heterologous sequence to encode a fusion protein. For example, for screening of peptide libraries for inhibitors of SCAH activity, it may be useful to encode a chimeric SCAH protein that is recognized by a commercially available antibody. A fusion protein may also be engineered to contain a cleavage site located between a SCAH sequence and the heterologous protein sequence, so that the SCAH may be cleaved and purified away from the heterologous moiety.

In an alternate embodiment of the invention, the coding sequence of scah could be synthesized, whole or in part, using chemical methods well known in the art (see Caruthers M H et al (1980) Nuc Acids Res Symp Ser 215–23, Horn T et al (1980) Nuc Acids Res Symp Ser 225–32, etc). Alternatively, the protein itself could be produced using chemical methods to synthesize a SCAH amino acid sequence, whole or in part. For example, peptide synthesis can be performed using various solid-phase techniques (Roberge J Y et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be purified by preparative high performance liquid chromatography (eg, Creighton (1983) *Proteins, Structures and Molecular Principles*, W H Freeman and Co, New York N.Y.). The composition of the synthetic peptides may be confirmed by amino acid analysis or sequencing (eg, the Edman degradation procedure; Creighton, supra). Additionally the amino acid sequence of SCAH, or any part thereof, may be altered during direct synthesis and/or combined using chemical methods with sequences from other proteins, or any part thereof, to produce a variant polypeptide.

Expression Systems

In order to express a biologically active SCAH, the nucleotide sequence encoding SCAH or its functional equivalent, is inserted into an appropriate expression vector, ie, a vector which contains the necessary elements for the transcription and translation of the inserted coding sequence.

Methods which are well known to those skilled in the art can be used to construct expression vectors containing a SCAH coding sequence and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual*, Cold Spring Harbor Press, Plainview N.Y. and Ausubel F M et al. (1989) *Current Protocols in Molecular Biology*, John Wiley & Sons, New York N.Y.

A variety of expression vector/host systems may be utilized to contain and express a scah coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla Calif.) or PSPORTI (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of scah, vectors based on SV40 or EBV may be used with an appropriate selectable marker.

In bacterial systems, a number of expression vectors may be selected depending upon the use intended for SCAH. For example, when large quantities of SCAH are needed for the induction of antibodies, vectors which direct high level expression of fusion proteins that are readily purified may be desirable. Such vectors include, but are not limited to, the multifunctional *E. coli* cloning and expression vectors such as BLUESCRIPT (Stratagene), in which the scah coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding SCAH may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi R M (1991) Results Probl Cell Differ 17:85–105) may be used. These constructs can be introduced into plant cells by direct DNA transformation or pathogen-mediated transfection. For reviews of such techniques, see Hobbs S or Murry L E in McGraw Yearbook of Science and Technology (1992) McGraw Hill New York N.Y., pp 191–196 or Weissbach and Weissbach (1988) Methods for Plant Molecular Biology, Academic Press, New York N.Y., pp 421–463.

An alternative expression system which could be used to express scah is an insect system. In one such system, *Autographa californica* nuclear polyhedrosis virus (AcNPV) is used as a vector to express foreign genes in *Spodoptera frugiperda* cells or in Trichoplusia larvae. The scah coding sequence may be cloned into a nonessential region of the virus, such as the polyhedrin gene, and placed under control of the polyhedrin promoter. Successful insertion of scah will render the polyhedrin gene inactive and produce recombinant virus lacking coat protein. The recombinant viruses are then used to infect *S. frugiperda* cells or Trichoplusia larvae in which SCAH is expressed (Smith et al (1983) J Virol 46:584; Engelhard E K et al (1994) Proc Nat Acad Sci 91:3224–7).

In mammalian host cells, a number of viral-based expression systems may be utilized. In cases where an adenovirus is used as an expression vector, a scah coding sequence may be ligated into an adenovirus transcription/translation complex consisting of the late promoter and tripartite leader sequence. Insertion in a nonessential E1 or E3 region of the viral genome will result in a viable virus capable of expressing SCAH in infected host cells. (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a scah sequence. These signals include the ATG initiation codon and adjacent sequences. In cases where scah, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express scah may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S C and R C Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C A et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the scah is inserted within a marker gene sequence, recombinant cells containing scah can be identified by the absence of marker gene function. Alternatively, a marker gene can be placed in tandem with a SCAH sequence under the control of a single promoter. Expression of the marker gene in response to induction or selection usually indicates expression of the tandem scah as well.

Alternatively, host cells which contain the coding sequence for scah and express SCAH may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the scah polynucleotide sequence can be detected by DNA-DNA or DNA-RNA hybridization or amplification using probes, portions or fragments of scah. Nucleic acid amplification based assays involve the use of oligonucleotides or oligomers based on the scah sequence to detect transformants containing scah DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of SCAH, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on SCAH is preferred, but a competitive binding assay may be employed. These and other assays are described, among other places, in Hampton R et al (1990, Serological Methods, a Laboratory Manual, APS Press, St Paul Minn.) and Maddox D E et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to scah include oligolabeling, nick translation, end-labeling or PCR amplification using a labeled nucleotide. Alternatively, the scah sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include US Pat. Nos. 3,817,837; 3,850,752; 3,939,350; 3,996,345; 4,277,437; 4,275,149 and 4,366,241. Also, recombinant immunoglobulins may be produced as shown in US Pat. No. 4,816,567 incorporated herein by reference.

Purification of SCAH

Host cells transformed with a scah nucleotide sequence may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing scah can be designed with signal sequences which direct secretion of SCAH through a prokaryotic or eukaryotic cell membrane. Other recombinant constructions may join scah to nucleotide sequence encoding a polypeptide domain which will facilitate purification of soluble proteins (Kroll D J et al (1993) DNA Cell Biol 12:441–53; cf discussion of vectors infra containing fusion proteins).

SCAH may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and SCAH is useful to facilitate purification.

In addition to recombinant production, fragments of SCAH may be produced by direct peptide synthesis using solid-phase techniques (cf Stewart et al (1969) Solid-Phase Peptide Synthesis, WH Freeman Co, San Francisco; Merrifield J (1963) J Am Chem Soc 85:2149–2154). In vitro protein synthesis may be performed using manual techniques or by automation. Automated synthesis may be achieved, for example, using Applied Biosystems 431 A Peptide Synthesizer (Perkin Elmer, Foster City, Calif.) in accordance with the instructions provided by the manufacturer. Various fragments of SCAH may be chemically synthesized separately and combined using chemical methods to produce the full length molecule.

Uses of SCAH

The rationale for use of the nucleotide and peptide sequences disclosed herein is based on the structural homologies among stem cell antigens as illustrated in FIG. 3 and functional similarities among LY-6 family proteins as reported by Classon B J and L Coverdale (supra) and Katz et al (supra).

Since a high level of expression of stem cell antigens is correlated with tumors from a variety of tissues and a more malignant phenotype, the SCAH-1 and SCAH-2 proteins can be used to identify antibodies, antagonists and inhibitors which would diminish the efficiency of local tumor growth and development without inducing cell proliferation. Additionally, SCAH antibodies, antagonists or inhibitors could be used to intervene in the alloresponses associated with transplant rejection and autoimmune diseases such as lupus nephritis.

SCAH Antibodies

SCAH-specific antibodies are useful for the diagnosis of conditions and diseases associated with expression of SCAH. Such antibodies include, but are not limited to, polyclonal, monoclonal, chimeric, single chain, Fab fragments and fragments produced by a Fab expression library. SCAH for antibody induction does not require biological activity; however, the protein fragment, or oligopeptide must be antigenic. Peptides used to induce specific antibodies may have an amino acid sequence consisting of at least five amino acids, preferably at least 10 amino acids. They should mimic a portion of the amino acid sequence of the natural protein and may contain the entire amino acid sequence of a small, naturally occurring molecule. Short stretches of SCAH amino acids may be fused with those of another protein such as keyhole limpet hemocyanin and antibody produced against the chimeric molecule. Neutralizing antibodies, ie, those which inhibit dimer formation, are especially preferred for diagnostics and therapeutics.

For the production of antibodies, various hosts including goats, rabbits, rats, mice, etc may be immunized by injection with SCAH or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to SCAH may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce SCAH-specific single chain antibodies.

Antibodies may also be produced by inducing In vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for SCAH may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Muse W D et al (1989) Science 256:1275–1281).

A variety of protocols for competitive binding or immunoradiometric assays using either polyclonal or monoclonal antibodies with established specificities are well known in the art. Such immunoassays typically involve the formation of complexes between SCAH and its specific antibody and the measurement of complex formation. A two-site, monoclonal-based immunoassay utilizing monoclonal antibodies reactive to two noninterfering epitopes on a specific SCAH protein is preferred, but a competitive binding assay may also be employed. These assays are described in Maddox D E et al (1983, J Exp Med 158:1211).

Diagnostic Assays Using SCAH Specific Antibodies

Particular SCAH antibodies are useful for the diagnosis of conditions or diseases characterized by expression of SCAH or in assays to monitor patients being treated with SCAH, agonists or inhibitors. Diagnostic assays for SCAH include methods utilizing the antibody and a label to detect SCAH in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring SCAH, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on SCAH is preferred, but a competitive binding assay may be employed. These assays are described, among other places, in Maddox, D E et al (supra).

In order to provide a basis for diagnosis, normal or standard values for SCAH expression must be established. This is accomplished by combining body fluids or cell extracts taken from normal subjects, either animal or human, with antibody to SCAH under conditions suitable for complex formation which are well known in the art. The amount of standard complex formation may be quantified by comparing various artificial membranes containing known quantities of SCAH with both control and disease samples from biopsied tissues. Then, standard values obtained from normal samples may be compared with values obtained from samples from subjects potentially affected by disease. Deviation between standard and subject values establishes the presence of disease state.

Drug Screening

SCAH, its catalytic or antigenic fragments or oligopeptides, can be used for screening therapeutic compounds in any of a variety of drug screening techniques. The fragment employed in such a test may be free in solution, affixed to a solid support, borne on a cell surface, or located intracellularly. The formation of binding complexes, between SCAH and the agent being tested, may be measured.

Another technique for drug screening which provides for high throughput screening of compounds having suitable binding affinity to the SCAH is described in detail in "Determination of Amino Acid Sequence Antigenicity" by Geysen H N, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of SCAH and washed. Bound SCAH is then detected by methods well known in the art. Purified SCAH can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding SCAH specifically compete with a test compound for binding SCAH. In this manner, the antibodies can be used to detect the presence of any peptide which shares one or more antigenic determinants with SCAH.

Uses of the Polynucleotide Encoding SCAH

A polynucleotide, scah, or any part thereof, may be used for diagnostic and/or therapeutic purposes. For diagnostic purposes, the scah of this invention may be used to detect and quantitate gene expression in biopsied tissues in which expression of SCAH may be implicated. The diagnostic assay is useful to distinguish between absence, presence, and excess expression of scah and to monitor regulation of scah levels during therapeutic intervention. Included in the scope of the invention are oligonucleotide sequences, antisense RNA and DNA molecules, and PNAs.

Because members of the LY-6 family have been shown to block interleukin 2 (IL-2) secretion, the SCAH proteins disclosed herein may play similar roles in cell-mediated immunity and may be useful as anticancer agents. If scah-1 or scah-2 prevent IL-2 activity, then antisense or PNA molecules which interfere with the expression of naturally occurring scah-1 or scah-2 would help restore T and NK cell proliferation as well as the tumor lysing activity of NK cells. Such antisense or PNA molecules may also be used to treat metastatic melanoma and renal cell carcinoma.

Another aspect of the subject invention is to provide for hybridization or PCR probes which are capable of detecting polynucleotide sequences, including genomic sequences, encoding SCAH or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring scah, alleles or related sequences.

Such probes may also be used for the detection of related encoding sequences and should preferably contain at least 50% of the nucleotides from any of these SCAH encoding sequences. The hybridization probes of the subject invention may be derived from the nucleotide sequence of the SEQ ID NOs:3 and 4 or from genomic sequence including promoter, enhancer elements and introns of the naturally occurring scah. Hybridization probes may be labeled by a variety of reporter groups, including radionuclides such as $^{32}P$ or $^{35}S$, or enzymatic labels such as alkaline phosphatase coupled to the probe via avidin/biotin coupling systems, and the like.

Other means for producing specific hybridization probes for scah DNAs include the cloning of nucleic acid sequences encoding SCAH or SCAH derivatives into vectors for the production of mRNA probes. Such vectors are known in the art, are commercially available and may be used to synthesize RNA probes in vitro by means of the addition of the appropriate RNA polymerase as T7 or SP6 RNA polymerase and the appropriate radioactively labeled nucleotides.

It is now possible to produce a DNA sequence, or portions thereof, encoding a SCAH and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a scah sequence or any portion thereof.

Diagnostics

Polynucleotide sequences encoding SCAH may be used for the diagnosis of conditions or diseases with which the expression of SCAH is associated. For example, polynucleotide sequences encoding SCAH may be used in hybridization or PCR assays of fluids or tissues from biopsies to detect scah expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

The nucleotide sequences may be used to construct an assay to detect activation or induction of SCAH associated with malignant tumors. The nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with the nucleotide sequences in the sample.

Such assays may be also be used to evaluate the efficacy of a particular therapeutic treatment regime in animal studies, in clinical trials, or in monitoring the treatment of an individual patient. In order to provide a basis for the diagnosis of disease, a normal or standard profile for scah expression must be established. This is accomplished by combining body fluids or cell extracts taken from normal subjects, either animal or human, with scah, or a portion thereof, under conditions suitable for hybridization or amplification. Standard hybridization may be quantified by comparing the values obtained for normal subjects with a dilution series of scah run in the same experiment where a known amount of purified scah is used. Standard values obtained from normal samples may be compared with values obtained from samples from patients affected by scah-associated diseases. Deviation between standard and subject values establishes the presence of disease.

Once disease is established, a therapeutic agent is administered; and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR as described in U.S. Pat. Nos. 4,683,195 and 4,965,188 provides additional uses for oligonucleotides based upon the scah sequence. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods to quantitate the expression of a particular molecule include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. For example, the presence of scah in extracts of biopsied tissues may indicate the onset of cancer. A definitive diagnosis of this type may allow health professionals to begin aggressive treatment and prevent further worsening of the condition. Similarly, assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutics

The polynucleotides disclosed herein may be useful in the treatment of conditions associated with the tissues used to construct the cDNA libraries (shown in the Sequence ID Listing) which contained partial scah sequences. These include, but are not limited to, conditions such as leukemias and cancers of the bladder, breast, lung, ovary, prostate and uterus.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antiscah. See, for example, the techniques described in Maniatis et al (supra) and Ausubel et al (supra).

The polynucleotides comprising full length cDNA sequence and/or its regulatory elements enable researchers to use scah as an investigative tool in sense (Youssoufian H and H F Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding SCAH can be turned off by transfecting a cell or tissue with expression vectors which express high levels of the desired fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of scah, ie, the promoters, enhancers, and introns. Oligonucleotides derived from the transcription initiation site, eg, between –10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J E et al. (In: Huber B E and B I Carr (1994) *Molecular and Immunologic Approaches*, Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of scah.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding SCAH. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient as presented in U.S. Pat. Nos. 5,399,493 and 5,437,994, disclosed herein by reference. Delivery by transfection and by liposome are quite well known in the art.

Furthermore, the nucleotide sequences for scah disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for scah can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C M (1993; Blood Rev 7:127–34) and Trask B J (1991; Trends Genet 7:1 49–54).

The technique of fluorescent in situ hybridization of chromosome spreads has been described, among other places, in Verma et al (1988) Human Chromosomes: A Manual of Basic Techniques, Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a scah on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers are invaluable in extending genetic maps. A recent example of an STS based map of the human genome was recently published by the Whitehead-MIT Center for Genomic Research (Hudson T J et al. (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, agonists, antibodies, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be, dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that is known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in an acceptable carrier have been prepared, they can be placed in an appropriate container and labeled for treatment of an indicated condition. For administration of SCAH, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

It is contemplated, for example, that scah-1 or scah-2 antisense can be delivered in a suitable formulation to diminish the expression of the genomic sequence. Effective delivery and downregulation of gene expression would serve to suppress the highly malignant phenotype.

The examples below are provided to illustrate the subject invention and are not included for the purpose of limiting the invention.

EXAMPLES

I cDNA Library Construction and Plasmid Isolation

The THP1PLB2 cDNA library was constructed from the THP-1 human leukemic cell line derived from the blood of a 1-year-old boy with acute monocytic leukemia. Cells used for the PMA-induced library were cultured for 48 hr with 100 nm PMA diluted in DMSO and for the PMA+LPS library were cultured for 48 hr with 100 nm PMA in DMSO and for 4 hr with 1 µg/ml LPS. The control THP-1 cells represent monocytes, PMA-induced cells represent macrophages, and PMA+LPS-stimulated cells represent activated macrophages. All three cDNA libraries—control, PMA induced, and PMA+LPS stimulated—were custom constructed by Stratagene (La Jolla Calif.) essentially as described below.

Stratagene prepared the THP-1 cDNA libraries using oligo d(T) priming. Synthetic adapter oligonucleotides were ligated onto the cDNA molecules enabling them to be inserted into the UNI-ZAP vector system (Stratagene) and transfected into E. coli host strain XL1-BLUE (Stratagene). The quality of the cDNA library was screened using DNA probes, and then, the PBLUESCRIPT phagemid (Stratagene) was excised by the in vivo excision process, in which the host bacterial strain was co-infected with both the library phage and an f1 helper phage. Polypeptides or enzymes derived from both the library-containing phage and the helper phage nicked the DNA, initiated new DNA synthesis from defined sequences on the target DNA, and created a smaller, single stranded circular phagemid DNA molecule that included all DNA sequences of the pBluescript phagemid and the cDNA insert. The phagemid DNA was released from the cells and purified, and used to reinfect fresh host cells (SOLR, Stratagene) where double-stranded phagemid DNA was produced.

The phagemid was purified using the Miniprep Kit (Catalog No. 77468, Advanced Genetic Technologies Corporation, Gaithersburg, Md.). This kit is in the 96-well format and provides enough reagents for 960 purifications. Each kit is provided with a recommended protocol, which has been employed except for the following changes. First, the 96 wells are each filled with only 1 ml of sterile terrific broth with carbenicillin at 25 mg/L and glycerol at 0.4%. After the wells are inoculated, the bacteria are cultured for 24 hours and lysed with 60 µl of lysis buffer. A centrifugation step (2900 rpm for 5 minutes) is performed before the contents of the block are added to the primary filter plate. The optional step of adding isopropanol to TRIS buffer is not routinely performed. After the last step in the protocol, samples are transferred to a Beckman 96-well block for storage.

The BLADTUT02 cDNA library was constructed from cancerous bladder tissue removed from an 80-year-old Caucasian female who had undergone radical cystectomy following diagnosis of grade 3 (of 4) invasive transitional cell carcinoma, a 3×2.5×1 cm mass on the posterior wall of the bladder with extension into the trigone, perivesical fat and vaginal mucosal margin. Distal urethral margins and the left pelvic lymph node were found negative for tumor. Patient's history included diagnoses of malignant neoplasm of uterus, benign hypertension, atherosclerosis, and atrial fibrillation.

The frozen bladder tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7M CsCI cushion using a Beckman SW28 rotor in a Beckman L8-70M Ultracentrifuge (Beckman Instruments) for 18 hours at 25,000 rpm at ambient temperature. The RNA was extracted with acid phenol pH 4.7, precipitated using 0.3M sodium acetate and 2.5 volumes of ethanol, resuspended in RNAse-free water, and DNase treated at 37° C. The RNA extraction was-repeated with acid phenol pH 4.7 and precipitated with sodium acetate and ethanol as before. The mRNA was then isolated using the OLIGOTEX kit (QIAGEN, Inc.; Chatsworth Calif.) and used to construct the cDNA library.

The cDNA library was initiated using oligo d(T) priming. The cDNAs were treated with T4 polymerase and synthetic adapter oligonucleotides were ligated onto the cDNAs enabling them to be inserted directionally into the pINCY vector (Incyte Pharmaceuticals, Palo Alto Calif.) using Eco RI and NotI.

Plasmid DNA was released from the cells and purified using the REAL Prep 96 Plasmid Kit for Rapid Extraction Alkaline Lysis Plasmid Minipreps (Catalog #26173; QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, LIFE TECHNOLOGIES™) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

II cDNA Sequencing

The cDNAs were sequenced by the method of Sanger et al. (1975, J Mol Biol 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems.

III Homology Searching of cDNA Clones and Their Deduced Proteins

Each cDNA in the libraries was compared to sequences in GenBank using a search algorithm developed by Applied Biosystems and incorporated into the INHERIT™ 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

After the reading frame was determined, the nucleotide sequences of the Sequence Listing or amino acid sequences deduced from them were used as query sequences against databases such as GenBank, SwissProt, BLOCKS, and Pima II. These databases which contain previously identified and annotated sequences, were searched for regions of homology (similarity) using BLAST, which stands for Basic Local Alignment Search Tool (Altschul (1993,1990) supra).

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith et al. (1992, *Protein Engineering* 5:35–51), incorporated herein by reference, could have been used when dealing with primary sequence patterns and secondary structure gap penalties.

The BLAST approach, as detailed in Karlin et al. (1993; Proc Nat Acad Sci 90:5873–5877) and incorporated herein by reference, searched for matches between a query sequence and a database sequence. BLAST evaluated the statistical significance of any matches found, and reported only those matches that satisfy the user-selected threshold of significance, $10^{-25}$ for nucleotides and $10^{-14}$ for peptides.

IV Northern Analysis

Northern analysis is a laboratory technique for the hybridization of a labeled nucleotide sequence to a membrane on which RNAs from a particular cell type or tissue have been bound (Sambrook et al. supra).

Analogous computer techniques, also known as electronic northern analysis, have been developed to use BLAST (Altschul S F (1993,1990) supra) to search for identical or related molecules in nucleotide databases such as GenBank or the LIFESEQ™ database (Incyte). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match is exact within a 1–2% error; and at 70, the match is exact. Homologous molecules are usually identified by selecting those which show product scores between 15 and 40, although lower scores may identify related molecules.

V Extension of SCAH Sequences

The nucleic acid sequences disclosed herein are used to design oligonucleotide primers for extending a partial nucleotide sequence to full length or for obtaining 5' sequences from genomic libraries. The PCR method employs XL-PCR™ (Perkin Elmer) to amplify and extend nucleotide sequences. One primer is synthesized to initiate extension in the antisense direction (XLR) and the other is synthesized to extend sequence in the sense direction (XLF). Primers allow the extension of the known SCAH sequence "outward" generating amplicons containing new, unknown nucleotide sequence for the region of interest. The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

Either the original cDNA library or a human genomic library is used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 µl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQUICK (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent *E. coli* cells (in 40 µl of appropriate media) are transformed with 3 µl of ligation mixture and cultured in 80 µl of SOC medium (Sambrook J et al, supra). After incubation for one hour at 37° C., the whole transformation mixture is plated on Luria Bertani (LB)-agar (Sambrook J et al, supra) containing 2×Carb. The following day, several colonies are randomly picked from each plate and cultured in 150 µl of liquid LB/2×Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer and one or both of the gene specific primers used for the extension reaction are added to each well. Amplification is performed using the following conditions:

Step 1 94° C. for 60 sec
Step 2 94° C. for 20 sec

Step 3 55° C. for 30 sec
Step 4 72° C. for 90 sec
Step 5 Repeat steps 2–4 for an additional 29 cycles
Step 6 72° C. for 180 sec
Step 7 4° C. (and holding)

Aliquots of the PCR reactions are run on agarose gels together with molecular weight markers. The sizes of the PCR products are compared to the original partial cDNAs, and appropriate clones are selected, ligated into plasmid and sequenced.

VI Labeling of Hybridization Probes

Hybridization probes derived from SEQ ID NO:3 or SEQ ID NO:4 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of [g-$^{32}$P] adenosine triphosphate (Amersham, Chicago Ill.) and T4 polynucleotide kinase (DuPont NEN®, Boston Mass.). The labeled oligonucleotides are purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VII Antisense Molecules

The scah sequences, or any part thereof, are used to inhibit in vivo or in vitro expression of naturally occurring scah. Although use of antisense oligonucleotides, comprising about 20 base-pairs of SCAH-1, is specifically described, essentially the same procedure is used with larger cDNA fragments or with SCAH-2.

An oligonucleotide based on the coding sequence of SCAH-1 as shown in FIG. 1 is used to inhibit expression of naturally occurring stem cell antigen. The complementary oligonucleotide is designed from the most unique 5' sequence as shown in FIG. 1 and used either to inhibit transcription by preventing promoter binding to the upstream nontranslated sequence or translation of a scah-1 transcript by preventing the ribosome from binding.

Using an appropriate portion of the leader and 5' sequence of SEQ ID NO:3 (or SEQ ID NO:4), an effective antisense oligonucleotide would include any 15–20 nucleotides spanning the region which translates into the signal or 5' sequence which encodes the polypeptides as shown in FIGS. 1 and 2, respectively.

VIII Expression of SCAH

Expression of SCAH is accomplished by subcloning the cDNAs into appropriate vectors and transfecting the vectors into host cells. In the case of SCAH-1, the cloning vector, PSPORT1, previously used for the generation of the cDNA library is used to express SCAH in E. coli. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length SCAH. The signal sequence directs the secretion of SCAH into the bacterial growth media which is used directly in the following assay for activity.

IX SCAH-1 and SCAH-2 Activity

The SCAH proteins are assayed using LY-6 as a positive control for their ability to block interleukin 2 (IL-2) activation of NK cells (Fleming T J and T R Malek (1994) J Immunol 153:1955–62). IL-2 is incubated with natural killer cells and freshly isolated, solid tumor cells and lysis is detected using a phase microscope. Simultaneous administration of LY-6, SCAH-1 and SCAH-2 is observed to decrease or destroy the activation of NK cells and prevent or diminish lysis of the tumor cells.

In the alternative, the presence and distribution of SCAH-1 or SCAH-2 molecules in hematopoietic cell populations are analyzed using monoclonal antibodies and FACS technologies (Terstappen L et al. (1993) J Hematotherapy 2:431–447).

X Production of SCAH Specific Antibodies

SCAH proteins purified using PAGE electrophoresis (Maniatis, supra) are used to immunize rabbits using standard protocols and to produce antibodies. The amino acid sequence translated from scah-1 or scah-2 is analyzed using DNASTAR software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions is described by Ausubel F M et al (supra) and shown in FIGS. 4 and 5.

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel F M et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

Xl Purification of Naturally Occurring SCAH Using Specific Antibodies

Naturally occurring or recombinant stem cell antigens are purified by immunoaffinity chromatography using antibodies specific for SCAH-1 or SCAH-2. An immunoaffinity column is constructed by covalently coupling the particular SCAH antibody to an activated chromatographic resin such as CnBr-activated Sepharose (Pharmacia Biotech). After the coupling, the resin is blocked and washed according to the manufacturer's instructions.

Media containing SCAH-1 or SCAH-2 is passed over the immunoaffinity column, and the column is washed under conditions that allow the preferential absorbance of SCAH-1 or SCAH-2 (eg, high ionic strength buffers in the presence of detergent). The column is eluted under conditions that disrupt antibody/SCAH binding (eg, a buffer of pH 2–3 or a high concentration of a chaotrope such as urea or thiocyanate ion), and the particular SCAH is collected.

XII Identification of Molecules Which Interact with SCAH

SCAH, or biologically active fragments thereof, are labelled with $^{125}$I Bolton-Hunter reagent (Bolton, A E and Hunter, W M (1973) Biochem J 133:529). Candidate molecules previously arrayed in the wells of a 96 well plate are incubated with the labelled SCAH, washed and any wells with labelled SCAH complex are assayed. Data obtained using different concentrations of SCAH are used to calculate values for the number, affinity, and association of SCAH with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which-are obvious to those skilled in molecular biology or related fields are intended to be within the scope of the following claims.

What is claimed is:

1. A purified polynucleotide encoding a polypeptide with an amino acid sequence shown in SEQ ID NO:2.

2. The polynucleotide consisting of the nucleic acid sequence of SEQ ID NO:4, or its complement.

3. An expression vector comprising the polynucleotide of claim 1.

4. A host cell transformed with the expression vector of claim 3.

5. A method for producing a polypeptide with the amino acid sequence of SEQ ID NO:2, the method comprising the steps of:

a) culturing the host cell of claim 4 to allow expression of the polypeptide; and b) recovering the polypeptide from the host cell culture.

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 131 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: SCAH-1
        ( B ) CLONE:

( x i ) SEQUENCE DESCRIPTION: SEQ ID NO:1:

```
Met Lys Ile Phe Leu Pro Val Leu Leu Ala Ala Leu Leu Gly Val Glu
 1               5                  10                  15
Arg Ala Ser Ser Leu Met Cys Phe Ser Cys Leu Asn Gln Lys Ser Asn
            20                  25                  30
Leu Tyr Cys Leu Lys Pro Thr Ile Cys Ser Asp Gln Asp Asn Tyr Cys
        35                  40                  45
Val Thr Val Ser Ala Ser Ala Gly Ile Gly Asn Leu Val Thr Phe Gly
    50                  55                  60
His Ser Leu Ser Lys Thr Cys Ser Pro Ala Cys Pro Ile Pro Glu Gly
65                  70                  75                  80
Val Asn Val Gly Val Ala Ser Met Gly Ile Ser Cys Cys Gln Ser Phe
                85                  90                  95
Leu Cys Asn Phe Ser Ala Ala Asp Gly Gly Leu Arg Ala Ser Val Thr
               100                 105                 110
Leu Leu Gly Ala Gly Leu Leu Leu Ser Leu Xaa Pro Ala Leu Leu Arg
           115                 120                 125
Phe Gly Pro
       130
```

( 2 ) INFORMATION FOR SEQ ID NO:2:

( i ) SEQUENCE CHARACTERISTICS:
        ( A ) LENGTH: 123 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: SCAH-2

(B) CLONE:

(xi) SEQUENCE DESCRIPTION: SEQ ID NO:2:

```
Met Lys Ala Val Leu Leu Ala Leu Leu Met Ala Gly Leu Ala Leu Gln
 1               5                  10                  15

Pro Gly Thr Ala Leu Leu Cys Tyr Ser Cys Lys Ala Gln Val Ser Asn
                20                  25                  30

Glu Asp Cys Leu Gln Val Glu Asn Cys Thr Gln Leu Gly Glu Gln Cys
            35                  40                  45

Trp Thr Ala Arg Ile Arg Ala Val Gly Leu Leu Thr Val Ile Ser Lys
        50                  55                  60

Gly Cys Ser Leu Asn Cys Val Asp Asp Ser Gln Asp Tyr Tyr Val Gly
 65                  70                  75                  80

Lys Lys Asn Ile Thr Cys Cys Asp Thr Asp Leu Cys Asn Xaa Ser Gly
                85                  90                  95

Ala His Ala Leu Gln Pro Ala Ala Ala Ile Leu Ala Leu Leu Pro Ala
               100                 105                 110

Leu Gly Leu Leu Leu Trp Gly Pro Gly Gln Leu
               115                 120
```

(2) INFORMATION FOR SEQ ID NO:3:

(i) SEQUENCE CHARACTERISTICS:
        (A) LENGTH: 537 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: SCAH-1
        (B) CLONE:

(xi) SEQUENCE DESCRIPTION: SEQ ID NO:3:

```
NAGGANGGTG GGGGACCCAN GGGTCCAGAG CGCAGTTCGG GTCGGAGCTY CGWCCAGGCT    60
GCTGGTACCT GCGTCCGCCC GGCGAGCAGG ACAGGCTGCT TTGGTTTGTG ACCTCCAGGC   120
AGGACGGCCA TCCTCTCCAG AATGAAGATC TTCTTGCCAG TGCTGCTGGC TGCCCTTCTG   180
GGTGTGGAGC GAGCCAGCTC GCTGATGTGC TTCTCCTGCT TGAACCAGAA GAGCAATCTG   240
TACTGCCTGA AGCCGACCAT CTGCTCCGAC CAGGACAACT ACTGCGTGAC TGTGTCTGCT   300
AGTGCCGGCA TTGGGAATCT CGTGACATTT GGCCACAGCC TGAGCAAGAC CTGTTCCCCG   360
GCCTGCCCCA TCCCAGAAGG CGTCAATGTT GGTGTGGCTT CCATGGGCAT CAGCTGCTGC   420
CAGAGCTTTC TGTGCAATTT CAGTGCGGCC GATGGCGGGC TGCGGGCAAG CGTCACCCTG   480
CTGGGTGCCG GGCTGCTGCT GAGCCTGWTG CCGGCCCTGC TGCGGTTTGG CCCCTGA     537
```

(2) INFORMATION FOR SEQ ID NO:4:

(i) SEQUENCE CHARACTERISTICS:
        (A) LENGTH: 494 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: SCAH-2
        (B) CLONE:

(xi) SEQUENCE DESCRIPTION: SEQ ID NO:4:

```
GTGACCATGA  AGGCTGTGCT  GCTTGCCCTG  TTGATGGCAG  GCTTGGCCCT  GCAGCCAGGC     60

ACTGCCCTGC  TGTGCTACTC  CTGCAAAGCC  CAGGTGAGCA  ACGAGGACTG  CCTGCAGGTG    120

GAGAACTGCA  CCCAGCTGGG  GGAGCAGTGC  TGGACCGCGC  GCATCCGCGC  AGTTGGCCTC    180

CTGACCGTCA  TCAGCAAAGG  CTGCAGCTTG  AACTGCGTGG  ATGACTCACA  GGACTACTAC    240

GTGGGCAAGA  AGAACATCAC  GTGCTGTGAC  ACCGACTTGT  GCAACGSCAG  CGGGGCCCAT    300

GCCCTGCAGC  CGGCTGCCGC  CATCCTTGCG  CTGCTCCCTG  CACTCGGCCT  GCTGCTCTGG    360

GGACCCGGCC  AGCTATAGGC  TCTGGGGGGC  CCCGMTGCAG  CCCACACTGG  GTGTGGTGCC    420

CCAAGGCCTC  TGTGSCACTC  CTMACAGACC  TGGGCCCAGT  GGGAGSCTGT  CTCTNGGTTC    480

CTGAGGCACA  TCCT                                                          494
```

( 2 ) INFORMATION FOR SEQ ID NO:5:

( i ) SEQUENCE CHARACTERISTICS:
  ( A ) LENGTH: 136 amino acids
  ( B ) TYPE: amino acid
  ( C ) STRANDEDNESS: single
  ( D ) TOPOLOGY: linear ( i i ) MOLECULE TYPE: peptide ( v i i ) IMMEDIATE SOURCE:
  ( A ) LIBRARY: GenBank
  ( B ) CLONE: 434660

( x i ) SEQUENCE DESCRIPTION: SEQ ID NO:5:

```
Met Ser Ala Thr Ser Asn Met Arg Val Phe Leu Pro Val Leu Leu Ala
 1               5                  10                  15

Ala Leu Leu Gly Met Glu Gln Val His Ser Leu Met Cys Phe Ser Cys
             20                  25                  30

Thr Asp Gln Lys Asn Asn Ile Asn Cys Leu Trp Pro Val Ser Cys Gln
         35                  40                  45

Glu Lys Asp His Tyr Cys Ile Thr Leu Ser Ala Ala Ala Gly Phe Gly
     50                  55                  60

Asn Val Asn Leu Gly Tyr Thr Leu Asn Lys Gly Cys Ser Pro Ile Cys
 65                  70                  75                  80

Pro Ser Glu Asn Val Asn Leu Asn Leu Gly Val Ala Ser Val Asn Ser
                 85                  90                  95

Tyr Cys Cys Gln Ser Ser Phe Cys Asn Phe Ser Ala Ala Gly Leu Gly
                100                 105                 110

Leu Arg Ala Ser Ile Pro Leu Leu Gly Leu Gly Leu Leu Leu Ser Leu
             115                 120                 125

Leu Ala Leu Leu Gln Leu Ser Pro
         130                 135
```

( 2 ) INFORMATION FOR SEQ ID NO:6:

( i ) SEQUENCE CHARACTERISTICS:
  ( A ) LENGTH: 109 amino acids
  ( B ) TYPE: amino acid
  ( C ) STRANDEDNESS: single
  ( D ) TOPOLOGY: linear ( i i ) MOLECULE TYPE: peptide ( v i i ) IMMEDIATE SOURCE:
  ( A ) LIBRARY: GenBank
  ( B ) CLONE: 1199651

( x i ) SEQUENCE DESCRIPTION: SEQ ID NO:6:

```
Met Ser Thr Thr Ser Ser Met Arg Val Phe Ser Ile Val Leu Gln Ala
```

```
    1                    5                         10                           15
His   Leu  Leu  Gly   Val  Glu  Leu  Val   Pro   Ser  Leu  Ile   Cys  Ser  Ser  Cys
                20                          25                         30

Thr   His  Gln  Lys   Ser  Asn  Ile  Asn   Pro   Pro  Trp  Pro   Val  Ala  Cys  Lys
                35                          40                         45

Asp   Thr  Gly  Asn   Tyr  Cys  Ile  Met   Leu   Phe  Ser  Ala   Val  Gly  Phe  Gly
                50                          55                         60

Asn   Val  Asn  Leu   Gly  Tyr  Thr  Leu   Asn   Thr  Gly  Cys   Ser  Gln  Ser  Cys
 65                         70                          75                        80

Pro   His  Glu  Asn   Ile  Asn  Ile  Asn   Pro   Gly  Val  Ala   Ser  Val  Asn  Ser
                85                                     90                    95

Tyr   Gln  Ser  Ser   Phe  Cys  Asn  Phe   Ser   Asn  Ala  Cys   Leu
                100                         105
```

( 2 ) INFORMATION FOR SEQ ID NO:7:

( i ) SEQUENCE CHARACTERISTICS:
        ( A ) LENGTH: 148 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: THP1PEB01
        ( B ) CLONE: 72518

( x i ) SEQUENCE DESCRIPTION: SEQ ID NO:7:

```
CCTGAAGCCG   ACCATCTGNT   CCGACCAGGN   CAACTACTGN   GTGACTGTGT   CTGCTAGTGC      60

CGGCATTTGG   AATCTTGTGC   CATTTNGACA   CAGCCTNAGC   AAGACCTNTT   CCCCGGCCTN     120

NCCCATCCCA   GAAGGNGTCA   ATNATNGT                                             148
```

( 2 ) INFORMATION FOR SEQ ID NO:8:

( i ) SEQUENCE CHARACTERISTICS:
        ( A ) LENGTH: 196 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: THP1PLB02
        ( B ) CLONE: 155838

( x i ) SEQUENCE DESCRIPTION: SEQ ID NO:8:

```
CGGACAGGCT   GCTTTGGTTT   GTNACCTCCA   GGCAGGACGG   CCATCCTCTC   CAGAATGAAG      60

ATCTTCTTGC   CANTGCTGCT   GGCTGCCCTT   CTNGGTGTGG   AGCGAGCCAG   CTCGCTGATG     120

TGCTTCTCCT   GCTTNAACCA   GAAGAGCAAT   CTGTACTGCC   TGAAGCCGAC   CATCTGCTCC     180

GACCAGGNCA   ACTACT                                                            196
```

( 2 ) INFORMATION FOR SEQ ID NO:9:

( i ) SEQUENCE CHARACTERISTICS:
        ( A ) LENGTH: 278 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:

( A ) LIBRARY: HNT2RAT01
( B ) CLONE: 486681

( x i ) SEQUENCE DESCRIPTION: SEQ ID NO:9:

| | | | | | | |
|---|---|---|---|---|---|---|
| GTTCGGGGAG | CTCGGCCAGG | CTGCTGGTAC | CTGCGTCCGC | CCGGCGAGCA | GGACAGGCTG | 60 |
| CTTTGGTTTG | TGACCTNCAG | GCAGGACGGC | CATCCTCTNC | AGAATGAAGA | TCTTCTTGCC | 120 |
| AGTGCTGCTG | GNTGCCCTTC | TGGGTGTGGA | GCGAGCCAGC | TNGCTGATGT | GCTTCTTCTG | 180 |
| CTTGAACCAG | AAGAGCAATC | TGTACTGCTG | AAGCCGACCA | TCTGTTCGAC | CAGGNCAACT | 240 |
| ACTGCGTGAC | TGTGTCTGCT | AGTGNCGGCA | TTGGGAAT | | | 278 |

( 2 ) INFORMATION FOR SEQ ID NO:10:

( i ) SEQUENCE CHARACTERISTICS:
        ( A ) LENGTH: 262 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: BRSTTUT01
        ( B ) CLONE: 604702

( x i ) SEQUENCE DESCRIPTION: SEQ ID NO:10:

| | | | | | | |
|---|---|---|---|---|---|---|
| GGTTCGGGGA | GCTCGGCCAG | GCTGCTGGTA | CCTGCGTCCG | CCCGGCGAGC | AGGACAGGCT | 60 |
| GCTTTGGTTT | GTGACCTCCA | GGCAGGACGG | CCATCCTCTC | CAGAATGAAG | ATCTTCTTGC | 120 |
| CAGTGCTGCT | GGCTGCCCTT | CTGGGTGTGG | AGCGAGCCAG | CTCGCTGATG | TGCTTCTCCT | 180 |
| GCTTGAACCA | GAAGAGCAAT | CTGTACTGCC | TGAAGCCGAC | CATCTGCTCC | GACCAGGACA | 240 |
| ACTACTGCGT | GACTGTGTCT | GC | | | | 262 |

( 2 ) INFORMATION FOR SEQ ID NO:11:

( i ) SEQUENCE CHARACTERISTICS:
        ( A ) LENGTH: 289 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: BRSTTUT01
        ( B ) CLONE: 606246

( x i ) SEQUENCE DESCRIPTION: SEQ ID NO:11:

| | | | | | | |
|---|---|---|---|---|---|---|
| GTTCGGGGAG | CTCGGCCAGG | CTGCTGGTAC | CTGCGTCCGC | CCGGCGAGCA | GGACAGGCTG | 60 |
| CTTTGGTTTG | TGACCTCCAG | GCAGGACGGC | CATCCTCTCC | AGAATGAAGA | TCTTCTTGCC | 120 |
| AGTGCTGCTG | GCTGCCCTTC | TGGGTGTGGA | GCGAGCCAGC | TCGCTGATGT | GCTTCTCCTG | 180 |
| CTTGAACCAG | AAGAGCAATC | TGTACTGCCT | GAAGCCGACC | ATCTGCTCCG | ACCAGGACAA | 240 |
| CTACTGCGTG | ACTGTGTCTG | CTAGTGCCGG | CATTGGGAAT | CTCGTGACA | | 289 |

( 2 ) INFORMATION FOR SEQ ID NO:12:

( i ) SEQUENCE CHARACTERISTICS:
        ( A ) LENGTH: 335 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
  ( A ) LIBRARY: BRSTNOT03
  ( B ) CLONE: 637479

( x i ) SEQUENCE DESCRIPTION: SEQ ID NO:12:

| | | | | | | |
|---|---|---|---|---|---|---|
| GTTCGGGGAG | CTCGGCCAGG | CTGCTGGTAC | CTGCGTCCGC | CCGGCGAGCA | GGACAGGCTG | 60 |
| CTTTGGTTTG | TGACCTCCAG | GCAGGACGGC | CATCCTNTCC | AGAATGAAGA | TCTTCTTGCC | 120 |
| AGTGCTGCTG | GCTGCCCTTC | TGGGTGTGGA | GCGAGCCAGC | TCGCTGATGT | GCTTCTNCTG | 180 |
| CTTGAACCAG | AAGAGCAATC | TGTACTGCCT | GAAGCCGACC | ATCTGCTCCG | ACCAGGACAA | 240 |
| CTACTGCGTG | ACTGTGTCTG | CTAGTGCCGG | CATTGGGAAT | CTCGTGACAT | TTGGNCACAG | 300 |
| CTGAGCAAGA | CCTGTTNCCC | GGNCTGCCCC | ATNCG | | | 335 |

( 2 ) INFORMATION FOR SEQ ID NO:13:

( i ) SEQUENCE CHARACTERISTICS:
    ( A ) LENGTH: 261 base pairs
    ( B ) TYPE: nucleic acid
    ( C ) STRANDEDNESS: single
    ( D ) TOPOLOGY: linear ( i i ) MOLECULE TYPE: cDNA ( v i i ) IMMEDIATE SOURCE:
    ( A ) LIBRARY: BRSTNOT03
    ( B ) CLONE: 641178

( x i ) SEQUENCE DESCRIPTION: SEQ ID NO:13:

| | | | | | | |
|---|---|---|---|---|---|---|
| GGTTCGGGGA | GCTCGGCCAG | GCTGCTGGTA | CCTGCGTCCG | CCCGGCGAGC | AGGACAGGCT | 60 |
| GCTTTGGTTT | GTGACCTNCA | GGCAGGACGG | CCATCCTCTC | CAGAATGAAG | ATCTTNTTGC | 120 |
| CAGTGCTNCT | NGCTGCCCTT | CTGGGTGTGG | AGCGAGCCAG | CTNGCTGATG | TGCTTCTTCT | 180 |
| GCTTGAACCA | GAAGAGCAAT | CTGTACTGTC | TGAAGCCGAC | CATTTGCTNC | GACCAGGNCA | 240 |
| ACTACTGTGT | GACTGTNTNT | T | | | | 261 |

( 2 ) INFORMATION FOR SEQ ID NO:14:

( i ) SEQUENCE CHARACTERISTICS:
    ( A ) LENGTH: 287 base pairs
    ( B ) TYPE: nucleic acid
    ( C ) STRANDEDNESS: single
    ( D ) TOPOLOGY: linear ( i i ) MOLECULE TYPE: cDNA ( v i i ) IMMEDIATE SOURCE:
    ( A ) LIBRARY: BRSTNOT03
    ( B ) CLONE: 642012

( x i ) SEQUENCE DESCRIPTION: SEQ ID NO:14:

| | | | | | | |
|---|---|---|---|---|---|---|
| AAGCCGACCA | TCTGCTCCGA | CCAGGACAAC | TACTGCGTGA | CTGTGTCTGC | TAGTGCCGGC | 60 |
| ATTGGGAATC | TCGTGACATT | TGGCCACAGC | CTGAGCAAGA | CCTGTTCCCC | GGCCTGCCCC | 120 |
| ATCCCAGAAG | GCGTCAATGT | TGGTGTGGCT | TCCATGGGNA | TCAGCTGCTG | CCAGAGCTTT | 180 |
| CTGTGCAATT | TCAGTGCGGC | CGATGGCGGG | CTGCGGGCAA | GCGTCACCCT | GCTGGGTGCC | 240 |
| GGGCTGCTGC | TGAGCTGCTG | CCGGCCCTGC | TGCGGTTTGG | CCCCTGA | | 287 |

( 2 ) INFORMATION FOR SEQ ID NO:15:

( i ) SEQUENCE CHARACTERISTICS:
    ( A ) LENGTH: 294 base pairs
    ( B ) TYPE: nucleic acid
    ( C ) STRANDEDNESS: single
    ( D ) TOPOLOGY: linear ( i i ) MOLECULE TYPE: cDNA ( v i i ) IMMEDIATE SOURCE:
    ( A ) LIBRARY: LUNGTUT02
    ( B ) CLONE: 690697

( x i ) SEQUENCE DESCRIPTION: SEQ ID NO:15:

| | | | | | |
|---|---|---|---|---|---|
| AGGANGGTGG | GGGACCCANG | GGTCCGGCCA | NGGGTCCGAG | NTTCGGCAAG | GTNCTGGTAN | 60 |
| CTGCGTNCGG | CCGGCGAGCA | GGACANGNTG | CTTTGGTTTG | TGACTNCAGG | NAGGACGGCC | 120 |
| ATNCTTNCAG | AATTAAGATC | TTNTTGCCAG | TGCTGNTGGC | TGCCCTTCTG | GGTGTNGAGC | 180 |
| GAGCCAGTNG | NTGATGTGNT | TNTTCTGCTT | GAACCAGAAG | AGCAATCTGT | ACTGCCTGAA | 240 |
| GCCGACCATG | TGGTTCGACC | AGGGCAACTA | NTGCGTGACT | GTGTCTGTAG | TGNC | 294 |

( 2 ) INFORMATION FOR SEQ ID NO:16:

( i ) SEQUENCE CHARACTERISTICS:
    ( A ) LENGTH: 266 base pairs
    ( B ) TYPE: nucleic acid
    ( C ) STRANDEDNESS: single
    ( D ) TOPOLOGY: linear ( i i ) MOLECULE TYPE: cDNA ( v i i ) IMMEDIATE SOURCE:
    ( A ) LIBRARY: LUNGNOT03
    ( B ) CLONE: 728784

( x i ) SEQUENCE DESCRIPTION: SEQ ID NO:16:

| | | | | | |
|---|---|---|---|---|---|
| TCCAGAGCGC | GCGAGGTTCG | GGGAGCTCGG | CCAGGCTGCT | GGTACCTGCG | TCCGCCCGGC | 60 |
| GGACAGGCTG | CTTTGGTTTG | TGACCTCCAG | GCAGGACGGC | CATCCTCTCC | AGAATGAAGA | 120 |
| TCTTCTTGCC | AGTGCTGCTG | GCTGCCCTTC | TGGGTGTGGA | GCGAGCCAGC | TCGCTGATGT | 180 |
| GCTTCTCCTG | CTTGAACCAG | AAGAGCAATC | TGTACTGCCT | GAAGCCGACC | ATCTGCTCCG | 240 |
| ACCAGGACAA | CTACTGNGTG | ACTGTG | | | | 266 |

( 2 ) INFORMATION FOR SEQ ID NO:17:

( i ) SEQUENCE CHARACTERISTICS:
    ( A ) LENGTH: 280 base pairs
    ( B ) TYPE: nucleic acid
    ( C ) STRANDEDNESS: single
    ( D ) TOPOLOGY: linear ( i i ) MOLECULE TYPE: cDNA ( v i i ) IMMEDIATE SOURCE:
    ( A ) LIBRARY: OVARNOT03
    ( B ) CLONE: 797584

( x i ) SEQUENCE DESCRIPTION: SEQ ID NO:17:

| | | | | | |
|---|---|---|---|---|---|
| TNGGNCCNGG | TGNTGGTACC | GNGTCCGCCC | GGCGAGCAGA | CAGGCTGCTT | TGGTTTGTGA | 60 |
| CCTCCAGGNA | GGACGGCCAT | CCTCTCCAGA | ATGAAGATCT | TCTTGCCAGT | GCTGCTGGCT | 120 |
| GCCCTTCTGG | GTGTGGAGCG | AGCCANCTCG | CTGATGTGCT | TCTCCTGCTT | GAACCAGAAG | 180 |
| AGCAATCTGT | ACTGCCTGAA | GCCGACCATC | TGCTNCGACC | AGGNCAACTA | CTGCGTGACT | 240 |
| GTGTCTGCTA | GTGCCGGCAT | TGGGAATCTC | GTGACAATTG | | | 280 |

( 2 ) INFORMATION FOR SEQ ID NO:18:

( i ) SEQUENCE CHARACTERISTICS:
    ( A ) LENGTH: 275 base pairs
    ( B ) TYPE: nucleic acid
    ( C ) STRANDEDNESS: single -continued (D) TOPOLOGY: linear (ii) MOLECULE TYPE: cDNA (vii) IMMEDIATE SOURCE:
(A) LIBRARY: PROSTUT04
(B) CLONE: 831396

(xi) SEQUENCE DESCRIPTION: SEQ ID NO:18:

| | | | | | |
|---|---|---|---|---|---|
| AGTTNGGGGA | GCTCCGTCAG | GCTNCTGGTA | CCTGCGTCCG | CCCGGCGAGC | AGGACAGGNT | 60 |
| GCTTTANTTT | NTGACCTNCA | GGCAGGACGG | CCATNCTATN | CAGAATGAAG | ATCTTATTGC | 120 |
| CANTGCTGNT | GGNTGNCCTT | NTGNGTGTNG | AGCGAGCCAG | NTCNATGATG | TGNTTNTCCT | 180 |
| GNTTGAACCA | AAGAGCAAT | NTGTANTGCC | TGAAGCCGAC | CATNTGNTCC | GACCAGGACA | 240 |
| ANTANTGCGT | GANTGTGTNT | GCTAGTGCCG | GCATT | | | 275 |

(2) INFORMATION FOR SEQ ID NO:19:

(i) SEQUENCE CHARACTERISTICS:
(A) LENGTH: 297 base pairs
(B) TYPE: nucleic acid
(C) STRANDEDNESS: single
(D) TOPOLOGY: linear (ii) MOLECULE TYPE: cDNA (vii) IMMEDIATE SOURCE:
(A) LIBRARY: BRSTNOT05
(B) CLONE: 897330

(xi) SEQUENCE DESCRIPTION: SEQ ID NO:19:

| | | | | | |
|---|---|---|---|---|---|
| GAACCAGAAG | AGCAATNTGT | ACTGCCTGAA | GCCGACCATN | TGCTNCGACC | AGGACAACTA | 60 |
| CTGCGTGACT | GTGTNTGCTA | GTGCCGGCAT | TGGGAATNTN | GTGACATTTG | GCCACAGCCT | 120 |
| GAGCAAGACC | TGTTCCCNGG | NCTGCCCCAT | CCCAGAAGGC | GTCAATGTTG | GTGTGGNTTC | 180 |
| CATGGGCATC | AGCTGCTGCC | AGAGCTTTNT | GTGCAATTTC | AGTGCGGCCG | ATGGNGGGCT | 240 |
| GNGGGCAAGC | GTCACCNTGN | TGGGTGCCGG | GNTGNTGNTG | AGCCTGGTGN | CGGCCCT | 297 |

(2) INFORMATION FOR SEQ ID NO:20:

(i) SEQUENCE CHARACTERISTICS:
(A) LENGTH: 126 amino acids
(B) TYPE: amino acid
(C) STRANDEDNESS: single
(D) TOPOLOGY: linear (ii) MOLECULE TYPE: peptide (vii) IMMEDIATE SOURCE:
(A) LIBRARY: GenBank
(B) CLONE: 509840

(xi) SEQUENCE DESCRIPTION: SEQ ID NO:20:

```
Met Lys Ala Phe Leu Phe Ala Val Leu Ala Ala Val Leu Cys Val Glu
 1               5                  10                  15

Arg Ala His Thr Leu Ile Cys Phe Ser Cys Ser Asp Ala Ser Ser Asn
                20                  25                  30

Trp Ala Cys Leu Thr Pro Val Lys Cys Ala Glu Asn Glu Glu His Cys
                35                  40                  45

Val Thr Thr Tyr Val Gly Val Gly Ile Gly Gly Lys Ser Gly Gln Ser
                50                  55                  60

Ile Ser Lys Gly Cys Ser Pro Val Cys Pro Ser Ala Gly Ile Asn Leu
65                  70                  75                  80

Gly Ile Ala Ala Ala Ser Val Tyr Cys Cys Asp Ser Phe Leu Cys Asn
```

|  | 85 | | | | 90 | | | | 95 | | | |
|---|---|---|---|---|---|---|---|---|---|---|---|---|

Ile Ser Gly Ser Ser Ser Val Lys Ala Ser Tyr Ala Val Leu Ala Leu
                100                 105                 110
Gly Ile Leu Val Ser Phe Val Tyr Val Leu Arg Ala Arg Glu
        115                 120                 125

( 2 ) INFORMATION FOR SEQ ID NO:21:

( i ) SEQUENCE CHARACTERISTICS:
        ( A ) LENGTH: 286 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: UTRSNOT01
        ( B ) CLONE: 588615

( x i ) SEQUENCE DESCRIPTION: SEQ ID NO:21:

```
ATGGCAGGCT  TGGCCCTGCA  GCCAGGNACT  GCCCTGCTGT  GCTACTCCTG  CAAAGCCCAG      60
GTGAGCAACG  AGGACTGCCT  GCAGGTGGAG  AACTGCACCC  AGCTGGGGGA  GCAGTGCTGG     120
ACCGCGCGCA  TNCGGCAGTT  GGCCTNCTGA  CCGTCATCAG  CAAAGGCTGC  AGCTTGAACT     180
GCGTGGATGA  CTNACAGGAC  TACTACGTGG  GCAAGAAGAA  CATCACGTGC  TGTGACANCG     240
ACTTGTGCAA  NGGCANCGGG  GCCCATGCCC  TGCAGNCGGC  TNTCGC                     286
```

( 2 ) INFORMATION FOR SEQ ID NO:22:

( i ) SEQUENCE CHARACTERISTICS:
        ( A ) LENGTH: 251 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: UTRSNOT01
        ( B ) CLONE: 590328

( x i ) SEQUENCE DESCRIPTION: SEQ ID NO:22:

```
AANAGGTTAT  TAGGNGGGAA  NGAGGACNAN  NANGTGTTGN  GACANCGACT  TGTGCAACGG      60
CAGCGGGGNC  CATGCCCTGN  AGCCGGCTGC  CGGCATCCTT  GCGCTGNTNC  CTGCACTCGG     120
NCTGCTGCTC  TGGGGACCCG  GNCAGCTATA  GGCTCTGGGG  GGNCCCGATG  CAGCCCACAN     180
TGGGTGTGGT  GCCCCAAGGC  TTGTGGCANT  NNTAANAGAN  CTGGGNCCAG  TGGGAGGCTT     240
NTCTNGGTAA  A                                                              251
```

( 2 ) INFORMATION FOR SEQ ID NO:23:

( i ) SEQUENCE CHARACTERISTICS:
        ( A ) LENGTH: 288 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: BLADTUT02
        ( B ) CLONE: 1312529

( x i ) SEQUENCE DESCRIPTION: SEQ ID NO:23:

```
GTGACCATGA  AGGCTGTGCT  GCTTGCCCTG  TTGATGGCAG  GCTTGGCCCT  GCAGCCAGGC      60
```

```
ACTGCCCTGC  TGTGCTACTC  CTGCAAAGCC  CAGGTGAGCA  ACGAGGACTG  CCTGCAGGTG    120

GAGAACTGCA  CCCAGCTGGG  GGAGCAGTGC  TGGACCGCGC  GCATCCGCGC  AGTTGGCCTC    180

CTGACCGTCA  TCAGCAAAGG  CTGCAGCTTG  AACTGCGTGG  ATGACTCACA  GGACTACTAC    240

GTGGGCAAGA  AGAACATCAC  GTGCTGTGAC  ACCGACTTGT  GCAAGCCA                  288
```

(2) INFORMATION FOR SEQ ID NO:24:

(i) SEQUENCE CHARACTERISTICS:
        (A) LENGTH: 230 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: BLADTUT02
        (B) CLONE: 1314679

(xi) SEQUENCE DESCRIPTION: SEQ ID NO:24:

```
GTGCTGTGAC  ACCGACTTGT  GCAACGCCAG  CGGGGCCCAT  GCCCTGCAGC  CGGCTGCCGC     60

CATCCTTGCG  CTGCTCCCTG  CACTCGGCCT  GCTGCTCTGG  GGACCCGGCC  AGCTATAGGC    120

TCTGGGGGGC  CCCGCTGCAG  CCCACACTGG  GTGTGGTGCC  CCAGGCCTCT  GTGCCACTCC    180

TCACAGACCT  GGCCCAGTGG  GAGCCTGTCC  TGGTTCCTGA  GGCACATCCT                230
```

(2) INFORMATION FOR SEQ ID NO:25:

(i) SEQUENCE CHARACTERISTICS:
        (A) LENGTH: 232 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: BLADTUT02
        (B) CLONE: 1315052

(xi) SEQUENCE DESCRIPTION: SEQ ID NO:25:

```
TGACCATGAA  GGCTGTGCTG  CTTGCCCTGT  TGATGGCAGG  CTTGGCCCTG  CAGCCAGGCA     60

CTGCCCTGCT  GTGCTACTCC  TGCAAAGCCC  AGGTGAGCAA  CGAGGACTGC  CTGCAGGTGG    120

AGAACTGCAC  CCAGCTGGGG  GAGCAGTGCT  GGACCGCGCG  CATCCGCGCA  GTTGGCCTCC    180

TGACCGTCAT  CAACAAAAGG  CTGCAGCTTG  AACTGCGTGG  ATGACTCACA  GG            232
```

(2) INFORMATION FOR SEQ ID NO:26:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: BLADTUT02
        (B) CLONE: 1317088

(xi) SEQUENCE DESCRIPTION: SEQ ID NO:26:

```
CGGGGCCCAT  GCCCTGCAGC  CGGCTGCCGC  CATCCTTGCG  CTGCTCCCTG  CACTCGGCCT     60

GCTGCTCTGG  GGACCCG                                                       77
```